US010321675B2

(12) United States Patent
Campsen

(10) Patent No.: US 10,321,675 B2
(45) Date of Patent: *Jun. 18, 2019

(54) SUSPENDABLE ORGAN TRANSPLANT SYSTEM AND METHOD OF USE

(71) Applicant: Paul Jeffrey Campsen, Salt Lake City, UT (US)

(72) Inventor: Paul Jeffrey Campsen, Salt Lake City, UT (US)

(*) Notice: Subject to any disclaimer, the term of this patent is extended or adjusted under 35 U.S.C. 154(b) by 57 days.

This patent is subject to a terminal disclaimer.

(21) Appl. No.: 15/684,955

(22) Filed: Aug. 24, 2017

(65) Prior Publication Data

US 2018/0042218 A1 Feb. 15, 2018

Related U.S. Application Data

(63) Continuation of application No. 14/681,837, filed on Apr. 8, 2015, now Pat. No. 9,781,920.

(60) Provisional application No. 61/977,519, filed on Apr. 9, 2014.

(51) Int. Cl.
*A61F 2/00* (2006.01)
*A01N 1/02* (2006.01)
*A61F 7/02* (2006.01)
*A61F 7/10* (2006.01)

(52) U.S. Cl.
CPC ......... *A01N 1/0247* (2013.01); *A01N 1/0263* (2013.01); *A01N 1/0273* (2013.01); *A61F 2007/023* (2013.01); *A61F 2007/101* (2013.01)

(58) Field of Classification Search
CPC .. A01N 1/0247; A01N 1/0263; A01N 1/0273; A61J 1/00; A61J 1/10; A61J 1/14; A61J 1/1462; A61B 2050/314

USPC .................................................. 600/37
See application file for complete search history.

(56) References Cited

U.S. PATENT DOCUMENTS

| | | | |
|---|---|---|---|
| 3,881,990 A | 5/1975 | Burton | |
| 4,484,351 A | 11/1984 | De Leeuwe et al. | |
| 4,991,593 A | 2/1991 | LaVahn | |
| 5,671,983 A | 9/1997 | Miller et al. | |
| 7,316,922 B2 | 1/2008 | Streeter | |
| 8,956,370 B2 | 2/2015 | Taylor et al. | |
| 9,781,920 B2 * | 10/2017 | Campsen | A01N 1/0247 |
| 2015/0289940 A1 | 10/2015 | Campsen et al. | |

FOREIGN PATENT DOCUMENTS

EP 2120784 2/2017

OTHER PUBLICATIONS

CNN, New Transplant Technology Keeps Organs 'Alive' Outside Body, CNN, Apr. 25, 2013, available at http://www.cnn.com/2013/25/health/live-organ-transplants/.

* cited by examiner

*Primary Examiner* — John P Lacyk
(74) *Attorney, Agent, or Firm* — Pate Peterson PLLC; Brett Peterson

(57) ABSTRACT

The present invention relates to organ transplant systems used to keep organs chilled and viable as they are moved between patients. More specifically, the present invention both contains the organ and holds it in position during transplant surgery. Thus, there is no need for a member of the implant surgical team to hold the organ while it is being sewn into place.

21 Claims, 5 Drawing Sheets

SUSPENDABLE ORGAN TRANSPLANT SYSTEM AND METHOD OF USE

BACKGROUND OF THE INVENTION

State of the Art

The present invention relates to organ transplant systems used to hold organs as they are moved between patients.

There are a variety of situations in which organs from one donor are placed into the body of a recipient, and the number of such procedures is increasing. According to data from the United Network for Organ Sharing (UNOS), for example, more than 400,000 renal transplantations have been performed since the first successful renal transplantation in the 1950s. Innovative developments in technique allow organs such as the pancreas to be transplanted in order to correct defects in insulin production, restoring insulin production in Type 1 diabetics. With improved surgical techniques and immunosuppressive medications, outcomes after renal and extrarenal (liver, pancreas, lung, heart, pancreas) transplantation have continued to improve.

Most solid-organ transplantations are now performed as the therapeutic option of choice. In many cases, transplantation offers definitive treatment for a given disease entity. As a result, the list of indications for solid-organ transplantation has expanded considerably, placing increasing pressure on an already limited supply of donororgans.

At the same time, a shortage of organs for transplant remains a major problem for patients. The number of candidates on the waiting list continues to increase each year—close to 60,000 adults were on the kidney waiting list in 2011—while organ donation numbers remain flat. The average waiting time for a deceased donor kidney transplant now exceeds three years.

Additionally, many organs recovered for transplant are discarded, and discard rates are increasing. Living donation rates have been essentially unchanged for the past decade, despite public donation programs and awareness campaigns. Not all organs are sufficiently healthy for transplant, either due to damage, age, alcohol consumption, or either acute or systemic infection. The organs of individuals infected with Hepatitis C, for example, cannot be placed into uninfected recipients (although ground-breaking new procedures sometimes permit organs infected with Hepatitis C to be placed in other Hepatitis C-positive individuals.)

With such constraints, preservation of organs for transport between centers, and preservation of organs during transplantation, becomes crucial. However, the conflict between the need to rapidly remove, transport, and implant organs in order to minimize ischemia time, and the need to keep manual organ manipulation to a minimum, poses serious technical challenges.

Even extremely short periods of manual handling may irreversibly damage organs. One study found that thirteen minutes of gentle manual manipulation of rat livers after harvest and before transplantation decreased survival by 70%, and doubled areas of necrosis. (Schemmer, P. et al., Gentle in situ liver manipulation during organ harvest decreases survival after rat liver transplantation: role of Kupffer cells. TRANSPLANTATION 5 1015-20 (Apr. 27, 1998; 65(8))).

By contrast, a simple renal transplant procedure, without complications, may take between two and three hours. The kidney to be transplanted must be manually held above the incision by one surgeon, while another sutures the vein, artery, and ureter into place. During this time, the organ is removed from the chilled solution in which it was transported, and thus may warm, leading to greater tissue death and an increased number of cellular changes. Small movements while the organ is being held may result in tissue damage, or could tug at newly-placed sutures, and the organ may drip chilled solution onto the patient or into the incision.

Additionally, the surgical incision may be quite small and already crowded by the surgical frame that bolts to the table and holds the incision open. Thus it can be difficult for the two or more surgeons to work comfortably.

Transplant procedures for other organs may take even longer than a kidney transplant. Some organs have many attachments, such as veins, arteries, etc., that all must be sutured into correct positions.

Moreover, while an organ is being held, it is exposed to both dry air and potential contaminants. Presently, an organ must be periodically re-moistened while it is being held, although this tends to result in more dripping into the patient's incision.

Further, infection after transplantation is a constant concern, and a major cause of organ failure. Any infection in a post-operative patient can greatly extend the length of a hospital stay, and the concurrent risk of further hospital-acquired (nosocomial) illness. The greatest concern with early infection is that organisms can infect a graft or its vascular supply at suture sites, causing mycotic aneurysms or dehiscence. Transplant recipients may take antibiotics for six months or more after receiving an organ.

Although operating rooms are typically equipped with air handling and ventilation systems in order to keep microorganisms to an irreducible minimum, such rooms are not perfectly sterile. The patient, healthcare workers, and inanimate objects are all capable of introducing potentially infectious material onto the surgical field. Operating room air may contain microbial-laden dust, lint, skin squames, or respiratory droplets. It has been found that the microbial level in operating room air is directly proportional to the number of people moving about in the room, and that contamination risks increase with activities such as moving, talking, and exposing an organ to the air. Organ transplant surgeons must therefore work as quickly as possible, balancing speed against the need to ensure that grafts are optimally placed and stitched.

In addition to working quickly, surgeons must also make note of every piece of equipment entering and leaving an operating room, in order to reduce the chances that a sponge, clamp, or other hardware may be left inside the organ recipient's body cavity.

Thus, there is a need for an organ transplant system and method that substantially minimizes organ handling, while keeping the organ optimally chilled, moistened, and shielded from any contamination. It is desirable that such an organ transplant system is easy to use, includes few detachable pieces, and reduces crowding around an incision during organ transplant. It is also desirable to provide such an organ transplant system which is disposable, inexpensive, and easy to manufacture

SUMMARY OF THE INVENTION

It is an object of the present invention to provide an organ transplant sleeve system and method of use which does at least one of reducing the handling of organs before and during transplantation; holding the organ in desired position during grafting, and/or reducing the rate of infections during transplant.

The present invention may include a container which both contains the organ and holds it in position during transplant surgery. The organ's veins, arteries, nerves, and other connective portions may be freely accessible, while the organ itself remains chilled and cushioned in the container. After being sewn into place, the organ can be released from the container and placed into the body cavity of the transplant recipient. Thus, in accordance with one application of the present invention, there is no need for a member of the implant surgical team to hold the organ while it is being sewn into place.

In some embodiments, the container is a transplant sleeve which includes a temperature sensor to indicate when the organ should be returned to a hypothermic preservation solution.

Some embodiments feature a connector mechanism which may be latched onto a Bookwalter® (Symmetry Surgical, Antioch, Tenn.) retractor frame or other surgical retractor frame which holds open a transplant patient's incision.

According to some aspects of the present disclosure, the connector mechanism may allow the transplant sleeve's elevation above the incision to be adjusted, in order to bring the organ closer or move it away with precision. The connector mechanism may also swivel to keep it out of the doctor's way when suturing on either side of the organ.

Additionally, in some embodiments, the transplant sleeve contains or absorbs drips of preservation solution, so that the liquid does not fall from the organ into the incision where excess fluid might interfere with the suture procedure.

In some embodiments, the transplant sleeve is perforated, so that the entire sleeve can be pulled open to release the organ, once it is in place.

According to some aspects of the present disclosure, the bottom and sides of the transplant sleeve may be releasably or slideably opened, to release the organ once grafting is complete.

In some embodiments, the bottom of the transplant sleeve may be held together by a magnetic strip.

According to some aspects of the present disclosure, the transplant sleeve may be formed as a single piece of any suitable material, as may be well known in the art, including biocompatible plastics, other types of flexible synthetic materials or fabrics. A single piece of material may reduce the number of small objects used during the surgery, and may make it significantly easier to confirm remaining equipment after the transplant surgery. The transplant container or sleeve may be transparent, in order to facilitate visual checks of the organ.

In some embodiments, the transplant sleeve may be glove-shaped. In this configuration, the transplant sleeve may be inserted into the body cavity of a living individual and placed around an organ in order to chill the organ during surgery. For example, a stopped heart may be chilled while the heart's valves are operated on.

In some embodiments, the transplant sleeve may contain cold packs, in order to extend the length of time a surgery may safely proceed with a viable organ.

In some embodiments, the transplant sleeve may be disposable, in whole or in part.

According to one aspect of the present invention, the transplant sleeve may be transparent, in order to facilitate visual checks of the organ, and to aid in locating organ attachments such as veins, arteries, and the like.

According to another aspect of the present invention, the organ transplant sleeve may substantially prevent bacteria, fungi, or other organisms/contaminates from contacting an organ placed inside.

According to another aspect of the present invention, an inner, organ-contacting surface of the organ transplant sleeve may be formed of a material which limits the ability of bacteria to attach to the material, such as a thermoplastic such as poly methyl methacrylate ("PMMA"), cyanoacrylate compounds, or any other suitable material to which infectious agents have a reduced ability to attach or proliferate.

In one embodiment of the present invention, the organ transplant sleeve may be flexible, in order to accommodate differing sizes of transplanted organs.

In one embodiment the organ transplant sleeve may be double-walled, allowing a user to access and replace the cooling packs without disturbing the organ.

According to still another aspect of the present invention, the organ transplant sleeve may include ports or openings through which the veins, arteries, and other attachment points of an organ may be accessed, without disturbing or releasing the organ.

According to another aspect of the invention, the organ transplant sleeve may comprise an antibiotic, antifungal, or sterilizing compound.

In accordance with one aspect of the present invention, a method of reducing the handling of organs before and during transplant may comprise placing an organ in a compartment, hanging the compartment from a rack, accessing the organ's connecting points, grafting the attachment points in place, and releasing the organ from the compartment.

According to another aspect of the invention, an organ transplant system may include tearable components made of a biocompatible and bio-absorbable material such that, if any fragments come loose, these fragments can be left in the body.

According to still another aspect of the present disclosure, a clip or a slider is disclosed for opening the access ports in order to access an organ's connecting veins, arteries, or the like.

According to another aspect of the present disclosure, an organ transplant sleeve may be equipped with ports so that coolant may be circulated through the sleeve while the organ is being grafted into place.

In still another embodiment, the organ transplant sleeve may be placeable within the body cavity of an individual, in order to chill an organ of the individual, while surgical procedures are performed on the individual. For example, an organ transplant sleeve may be placed around the heart, while the heart's valves are replaced.

These and other aspects of the present invention are realized in a suspended organ transplant sleeve system and method of use as shown and described in the following figures and related description.

BRIEF DESCRIPTION OF THE DRAWINGS

Various embodiments of the present invention are shown and described in reference to the numbered drawings wherein.

Figure 1:
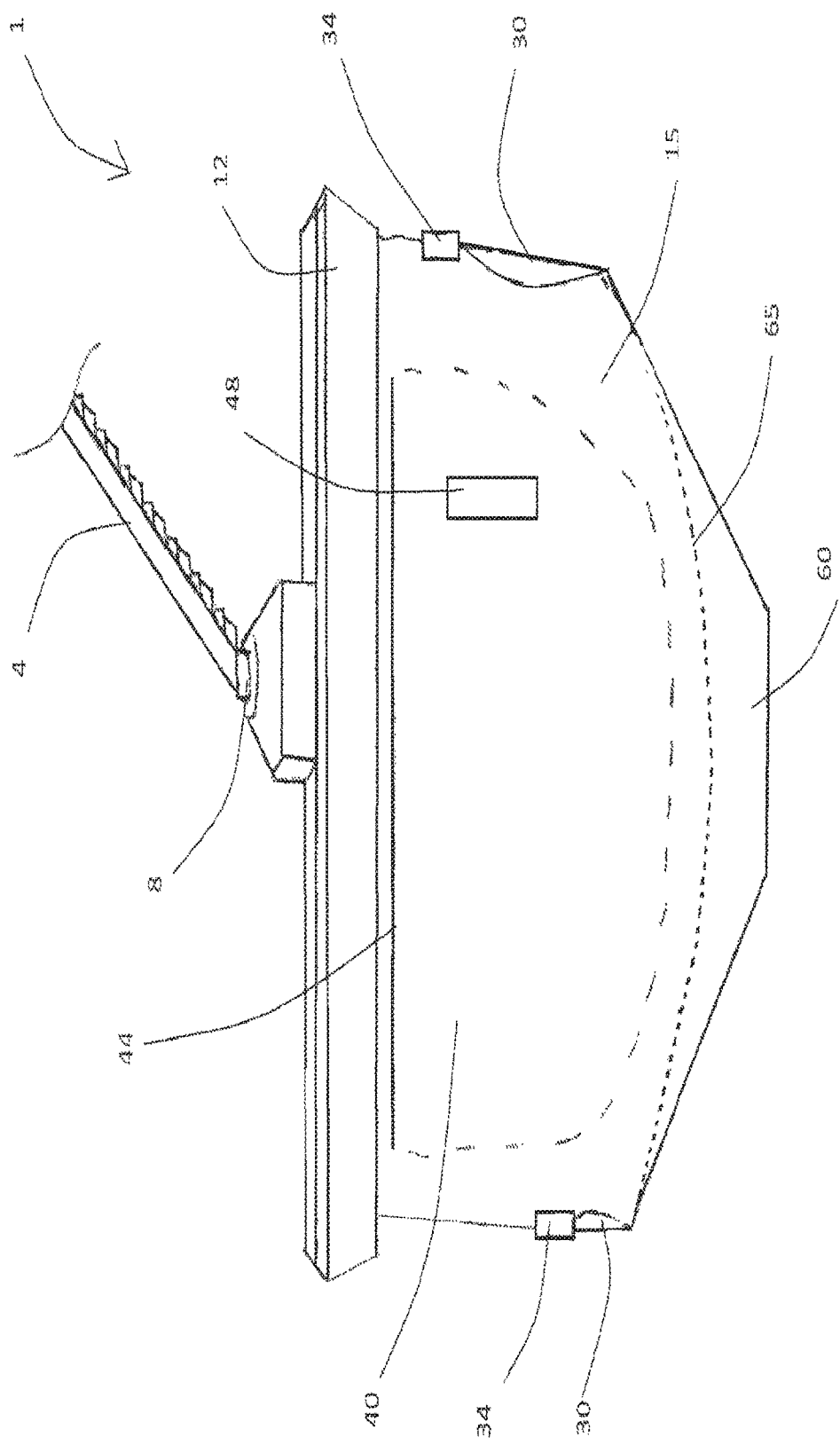
FIG. 1 illustrates one embodiment of the present disclosure, featuring a double-walled, padded, transplant sleeve, and tearable perforations through which an organ may be removed.

It will be appreciated that the drawings are illustrative and not limiting of the scope of the invention which is defined by the appended claims. The various elements of the invention accomplish various aspects and objects of the invention. It is appreciated that not every element of the invention can be clearly displayed in a single drawing, and as such not every drawing shows each element of the invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims. It will be appreciated that the various aspects of the suspended organ transplant systems discussed herein may be the same. Different reference numerals may be used to describe similar structures in the various suspended organ transplant systems for clarity purposes only.

Various aspects of the invention and accompanying drawings will now be discussed in reference to the numerals provided therein so as to enable one skilled in the art to practice the present invention. The skilled artisan will understand, however, that the methods described below can be practiced without employing these specific details, or that they can be used for purposes other than those described herein. Indeed, they can be modified and can be used in conjunction with products and techniques known to those of skill in the art in light of the present disclosure. Furthermore, it will be appreciated that the drawings may show aspects of the invention in isolation and the elements in one figure may be used in conjunction with elements shown in other figures.

Reference in the specification to "one configuration," "one embodiment" "one aspect" or "a configuration," "an embodiment" or "an aspect" means that a particular feature, structure, or characteristic described in connection with the configuration may be included in at least one configuration and not that any particular configuration is required to have a particular feature, structure or characteristic described therein unless set forth in the claim. The appearances of the phrase "in one configuration" or similar phrases in various places in the specification are not necessarily all referring to the same configuration, and may not necessarily limit the inclusion of a particular element of the invention to a single configuration, rather the element may be included in other or all configurations discussed herein. Thus it will be appreciated that the claims are not intended to be limited by the representative configurations shown herein. Rather, the various representative configurations are simply provided to help one of ordinary skill in the art to practice the inventive concepts claimed herein.

Furthermore, the described features, structures, or characteristics of embodiments of the present disclosure may be combined in any suitable manner in one or more embodiments. In the following description, numerous specific details may be provided, such as examples of products or manufacturing techniques that may be used, to provide a thorough understanding of embodiments of the invention. One skilled in the relevant art will recognize, however, that embodiments discussed in the disclosure may be practiced without one or more of the specific details, or with other methods, components, materials, and so forth. In other instances, well-known structures, materials, or operations may not be shown or described in detail to avoid obscuring aspects of the invention.

Before the present invention is disclosed and described in detail, it should be understood that the present invention is not limited to any particular structures, process steps, or materials discussed or disclosed herein. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of that aspect in the claims.

It should also be noted that, as used in this specification and the appended claims, singular forms such as "a," "an," and "the" may include the plural unless the context clearly dictates otherwise. Thus, for example, reference to "a bracket" may include an embodiment having one or more of such brackets, and reference to "the target plate" may include reference to one or more of such target plates.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The invention and accompanying drawings will now be discussed in reference to the numerals provided therein so as to enable one skilled in the art to practice the present invention. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Turning to FIG. 1, there is shown a front view of a suspendable organ transplant container, according to principles of the present invention. The transplant container may be sleeve-like in that it forms a case into which the organ to be transplanted fits. Thus, for convenience, the container will be generally referred to as a transplant sleeve, and is generally indicated at 1. The transplant sleeve 1 may include a connector mechanism 4. The connector mechanism 4 may be adapted to hook onto a surgical frame (not shown) placed around the patent. The surgical frame may be, for example, a Bookwalter® (Symmetry Surgical, Antioch, Tenn.) frame or any other surgical frame known to one of skill in the art, commonly used during a surgery to hold an incision open or to perform other surgical tasks.

The connector mechanism 4 may include a swivel 8, allowing the transplant sleeve 1 to be rotated to permit the surgeon to suture on either side of the organ.

The transplant sleeve 1 may be closed at the top with a clamp 12. The clamp may be, for example, a magnetic strip, an operable clamp, or bar into which the transplant sleeve 1 can be slid.

The transplant sleeve 1 further comprises a main body 15 and a port or main body opening 30, positioned to facilitate access to the veins, arteries, ducts, and other attachment portions of an organ (not shown). In some embodiments, the accessible port(s) 30 may be located in the center of the bottom end, allowing the organ's veins, arteries, and any other organ attachments to dangle down for easy access through the transplant sleeve 1. In other embodiments, the accessible opening(s) 30 may be fixed to a size suitable to allow access to the organ's veins, arteries or other necessary attachment points. In some embodiments, the operable ports 30 can be partly opened, enlarging the accessible opening to allow for easier access to the organ attachment points for different organs.

The main body or vessel 15 of the transplant sleeve 1 may be flexible in order to accommodate organs of varying sizes, or may be somewhat rigid in order to form an interior void or organ cavity adapted to receive an organ of a particular size and protect it from being bumped or otherwise injured. The main body 15 may be transparent in order to facilitate a visual check of the organ.

One advantage of the present invention is that, in some embodiments, the main body 15 can withstand being immersed in preservation solution for at least several hours. Thus, the organ can be harvested, placed in the transplant sleeve 1, and then the transplant sleeve 1 can be immediately packaged in chilled preservation solution prior to transport. Thus, the amount of manipulation of the organ between harvest and implantation surgery can be minimized.

In the embodiment shown in FIG. 1, the port openings 30 are positioned on the sides of the main body 15, and are operably openable by sliders 34 similar to those used along the top of ZIPLOC® bags. The sliders 34 can be placed in a closed position while the organ is transported, in order to protect the veins, arteries, ducts, and other attachment points of the organ. When each attachment point is needed for grafting, the port 30 can be opened with the slider 34, permitting access to the attachment point. Thus, the ports 30 permit access to the organ to be contained within the main body 15, through which transplant surgeons or other medical personnel may access the arteries, veins, and other features of an organ while the organ remains in the transplant sleeve 1.

It will be appreciated that the port 30 need not be opened with a slider 34; rather, the port 30 may be held closed with a tearable perforation, a patch of hook-and-loop material, releaseable adhesive, or any other reversible means of attachment known to one of skill in the art. The port 30 may be left open during organ transport, if desired. The individual ports 30 may also be labeled or colored, in order to indicate the orientation of the organ contained within the main body 15. For example, the port 30 positioned closest to a duct may be colored green to differentiate it from the port 30 positioned closest to an artery, and the like.

The main body 15 of the transplant sleeve 1 may also be equipped with a cold pack pocket 40. A cold pack pocket 40 may be present on one side of the suspendable organ transplant sleeve 1, may wrap around the organ transplant sleeve 1, or a cold pack pocket 40 may be located on both sides of the main body 15. In some embodiments, the pocket or pockets 40 are integral and contain saline or other fluid capable of chilling and cushioning an organ. In other embodiments the pocket 40 may have a cold pack opening 44, so that a cold pack (not shown) may be inserted or removed as necessary to maintain optimal organ temperature.

In some embodiments, the main body 15 of the transplant sleeve 1 includes a temperature indicator 48. The temperature indicator 48 may be a visual indicator, or may be a network-enabled sensor, which enables a user to track the temperature of an organ remotely, or while the organ is being transported.

In the pictured embodiment, the bottom portion 60 of the sleeve 1 is closed, in order to provide a drip reservoir, thus preventing the organ from dripping into an incision during transplant In the pictured embodiment, the main body 15 of the transplant sleeve 1 is interrupted by a tearable perforation 65 which connects each port 30. Thus, after an organ has been fully sutured into place, the organ transplant sleeve 1 may be easily pulled apart, releasing the organ without disturbing any of the sutures. The tearable perforation 65 may be located on only one side of the main body 15, and thus when the tearable perforation 65 is pulled apart, the suspendable organ transplant sleeve 1 will still be a single piece of material. This has the advantage of minimizing the number and variety of equipment needed for an organ transplant surgery, and reducing the labor required to confirm and count all remaining equipment, after the transplant surgery is completed.

In other embodiments, the transplant sleeve 1 may be disposable, reducing storage and sterilization costs.

In yet other embodiments, the main body 15 may be sized and shaped appropriately for a human kidney, or may be shaped to receive a variety of sizes of organs.

Figure 2C:
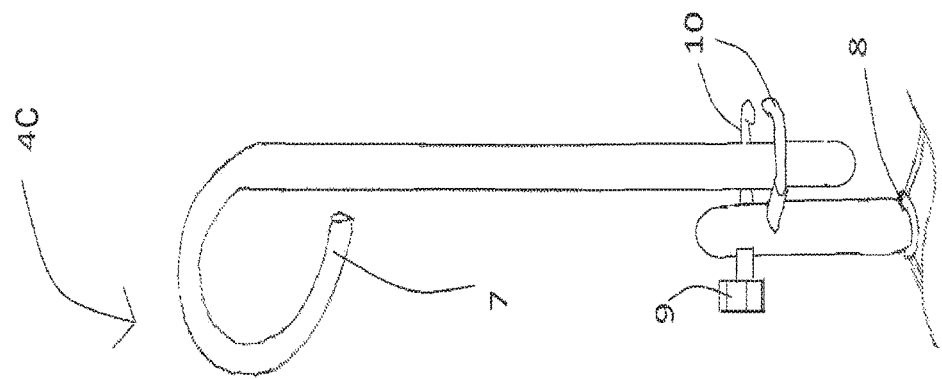
FIGS. 2a, 2b, and 2c illustrate three embodiments of a retractor frame attachment mechanism adapted to attach to a Bookwalter®, Omni®, and Synthes® frame, respectively, and which may include a swivel mechanism to allow the transplant sleeve to be raised, lowered, or swiveled from side to side.
Figure 2B:
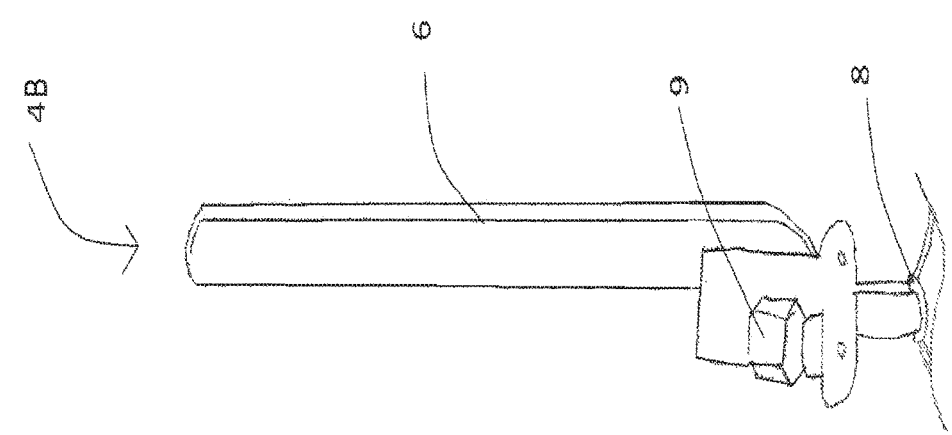
Figure 2A:
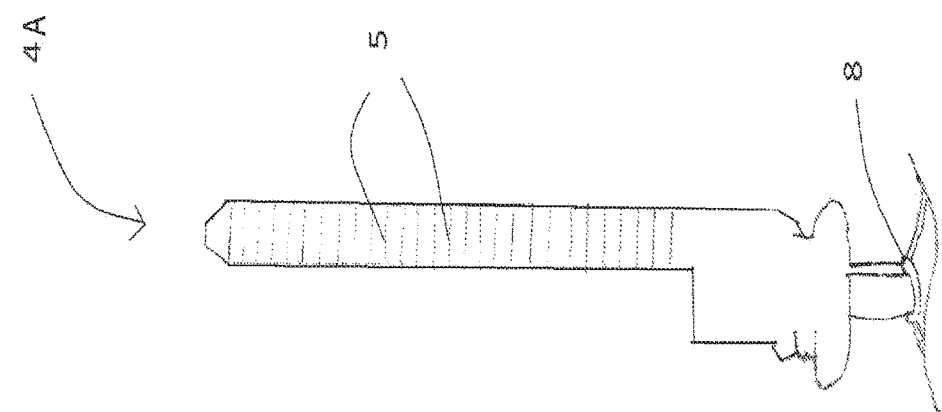

Now turning to FIGS. 2A, 2B, and 2C, there are shown several representative embodiments of connector mechanisms 4A, 4B, 4C, which may be used to suspend the organ transplant sleeve (not shown) from a surgical frame at a desired height. Connector mechanisms may be equipped with a swivel 8, so that the organ transplant sleeve may be turned to allow a surgeon to suture on either side of the organ. In the illustrated embodiments, the connector mechanism is adjustable, such that the organ can be releasably attached at a range of elevations above the surgical incision.

Turning to FIG. 2A specifically, a connector mechanism 4A may include ratcheting protrusions 5 which allow an organ transplant sleeve to be freely positioned on a frame with matching protrusions and clamps, such as a Bookwalter® frame.

In some embodiments, such as FIG. 2B, a connector mechanism 4B may include an integral clamp 9 and a slotted rod 6. Protrusions on a frame fit into the slotted rod 6. The integral clamp 9 can be tightened to compress the slotted rod 6 to engage the portion of the frame held within the slotted rod 6, thus holding it in place.

In some embodiments, the connector mechanism 4C may be a simple hooked rod 7, which can be hooked over a surgical frame. In such an embodiment, padded arms 10 may clamp around the hooked rod 7, and can be tightened or loosened by means of an integral screw 9. Regardless of which specific embodiment is used, the connector mechanisms 4A, 4B or 4C allow the transplant sleeve 1 to be held adjacent the transplant site to minimize the amount of handling to which the organ is subjected.

Figure 3:
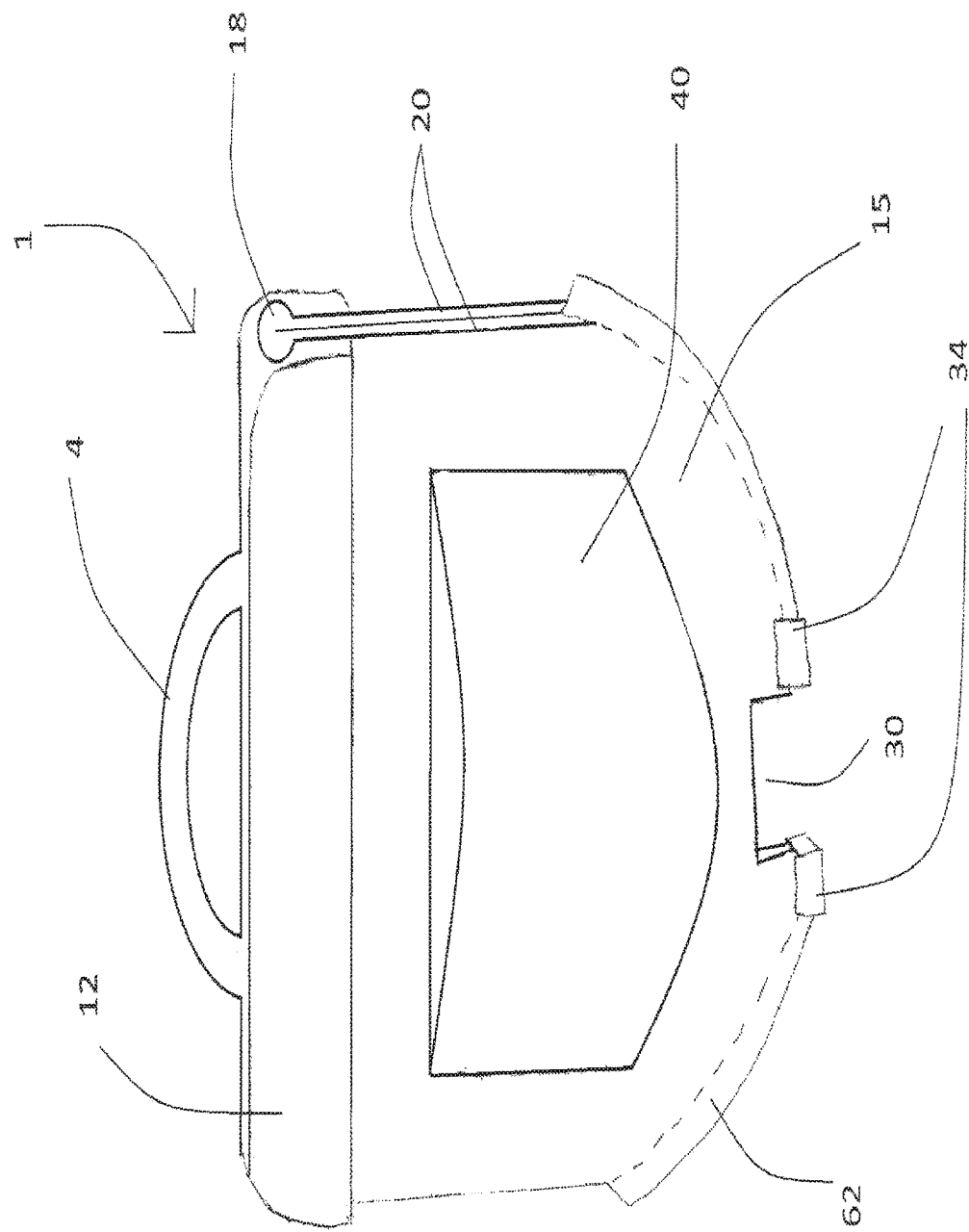
FIG. 3 illustrates one embodiment of the present invention, featuring a slideable bottom locking mechanism.

Turning now to FIG. 3, there is shown a slightly-angled view of a suspendable organ transplant sleeve, generally indicated at 1. In the pictured embodiment, the connector mechanism 4 is a simple handle or loop. The main body 15 is comprised of outer walls 20 which are joined together at a top joint 18. The top joint 18 is adapted to fit the clamp 12. In the present embodiment, the clamp 12 is a u-shaped holder with open ends, and the top joint 18 is thickened, so that the clamp 12 may be slid onto the top joint 18. Once in place, the suspendable organ transplant sleeve 1 cannot fall out of the clamp 12, because the thickness of the top joint 18 is too great to slip downwards out of the clamp 12.

As shown in FIG. 3, the organ transplant sleeve 1 may have a single port opening 30. The entire bottom may be openable to release the organ, once it is sutured into place, by drawing sliders 34 along closure tracks 62. It will be appreciated that any equivalent means of reversibly sealing the organ transplant sleeve 1 known to one of skill in the art may be employed, such as a perforated line, a releasable adhesive, and the like. It will also be appreciated that irreversible configurations may also be used in some situations.

Also shown is the cold pack pocket 40—in this case, the pocket 40 is shaped to receive a replaceable cold pack (not shown) which may be removed, chilled, and inserted again. In use a doctor or other health care professional takes an organ which is to be transplanted and places the organ within a void formed by the material forming the main body 15 of the transplant sleeve. This may be accomplished through an opening at the top which is later closed or through another opening in the body. It is preferred that the main body 15 is configured to allow disposition of the organ therein with minimal handling of the organ. Whatever opening is used to dispose the organ inside the main body 15 is then closed and a cooling agent may be added if not already present. The organ is then ready for transport Once in the operating room with the patient who will be receiving the organ, one or more of the openings may be opened to provide access to the organ while the transplant sleeve remains holding the organ, thereby minimizing potential injury to the organ. Once part of all of the veins and ducts are attached, the transplant sleeve 1 may be opened so as to allow the remainder of the organ to be removed from the sleeve.

Figure 4:
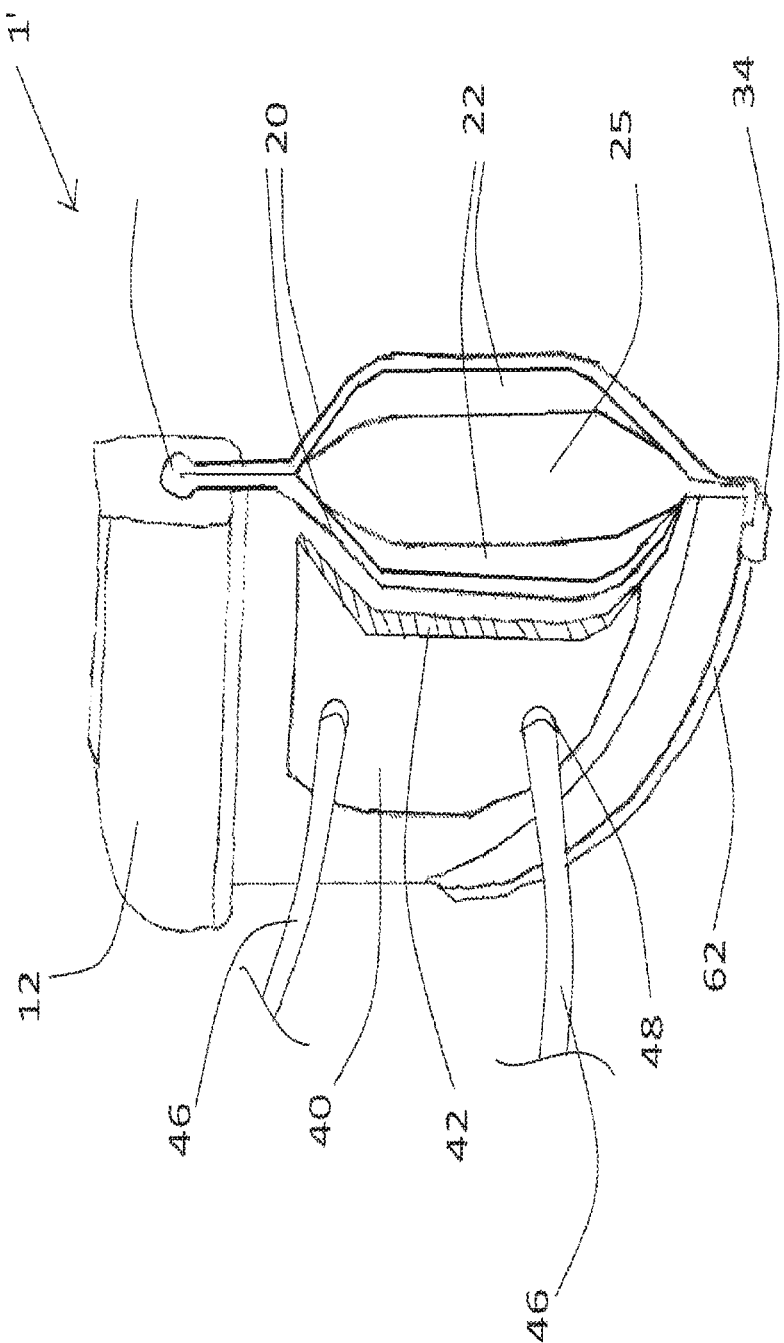
FIG. 4 illustrates a cut-away view of one embodiment of the present invention, featuring a cold pack pouch and interior padding, as well as a flexible sleeve structure.

Turning now to FIG. 4, there is shown a, cut-away view of an organ transplant sleeve, generally indicated at 1'. In the present embodiment, main body 15 is formed in part by outer walls 20 which are thickened at the top to form the top joint 18, which may be slid into the clamp 12 to selectively close the opening at the top of the sleeve 1' into which the organ is originally placed.

In the present embodiment, the outer walls 20 are somewhat stiffened, such that the void between the outer walls forms an organ cavity 25. The size of organ cavity 25 may be adapted to fit, for example, a mammal's kidney, heart, liver, or other organ requiring transplant.

As shown, the organ cavity 25 is padded by padded inner walls 22. The padded inner walls 22 may be insulated in order to keep the organ optimally chilled. The padded inner walls 22 may be filled with air or saline, and in some embodiments the inflation of the padded inner walls 22 may be adjusted after insertion of an organ, in order to prevent the organ from shifting during transport and surgery.

As shown, the padded internal walls 22 and the shaped external walls 20 cause the organ cavity 25 to narrow near the bottom. This has the advantage of preventing an organ placed within from slipping downwards while the organ transplant sleeve 1 is suspended from a surgical rack (not shown).

In the present embodiment, the cold pack pocket 40 may be an integral, closed, and recirculating chamber. The cold pack pocket may contain, for example, a chilled liquid or thin gel 42 which circulates via circulating tubes 46. Tubes 46 may be detachable, for example with twist-style luer lock adapters 48. The advantage therein is that the tubes 46 may be detached during organ transport. When the organ sleeve 1 is hung on a surgical rack for transplant, or if the surgery becomes lengthier than normal, the tubes 46 may be attached and chilled fluid may be circulated in order to maintain optimum organ temperature.

Also as shown in FIG. 4, the bottom of the organ transplant sleeve may be opened via pull slides or one or more port slides 34, drawn along closure tracks 62, thus releasing the organ. In such a manner, the organ is carefully held during transport and during the initial stages of implantation, while being easy for the surgeon to access.

Figure 5:
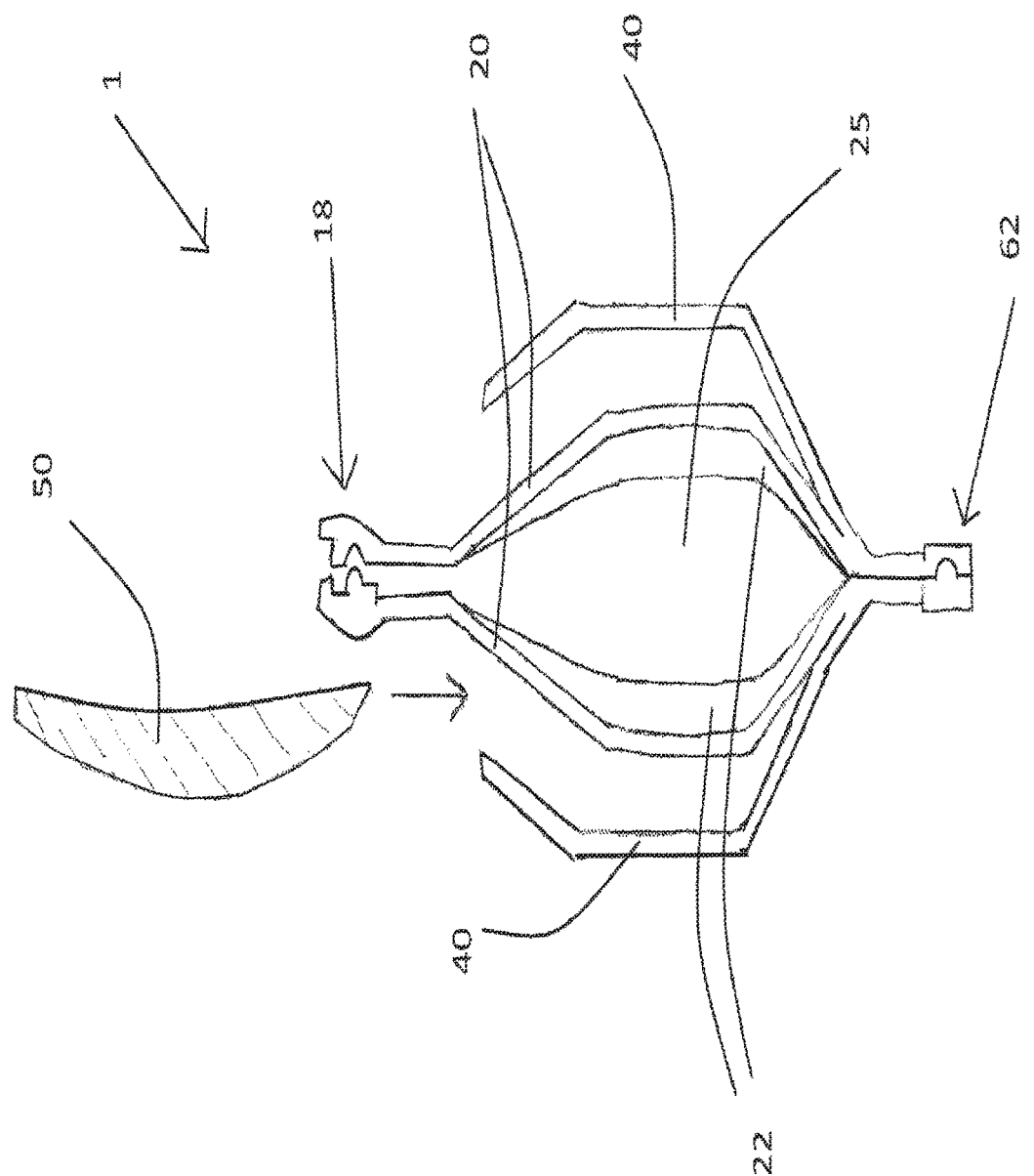
FIG. 5 illustrates a cross-sectional, partially exploded view of one embodiment of the present invention.

FIG. 5 illustrates a cross-sectional view of an organ transplant sleeve, generally indicated at 1, with the clamp (not shown) removed. The outer walls 20 may be formed in essentially two pieces joined along the sides, or by a single piece of material. The material may be open at the top but closeable by a top joint 18, and at the bottom by closure tracks 62. The top joint 18 may be constructed, for example, out of a deformable plastic, so that the two halves may be pressed tightly together. It will be appreciated that the two outer walls 20 may also be joined at the top by irreversible means, such as adhesive, ultrasonic welding or any other means known to one of skill in the art.

It is advantageous if the outer walls 20 are secured together at the top joint 18 immediately after the organ is harvested and placed inside, thus substantially preventing bacteria, fungi, and/or other contaminants from contacting the organ during both transport and recipient surgery. In some embodiments (FIG. 4, for example), the outer walls 20 are permanently attached at the top joint 18. In such embodiments, a harvested organ may be inserted by unzipping the closure tracks 62 at the bottom of the sleeve, inserting the organ, and zipping the closure tracks 62 into a closed position.

When joined at the bottom, the closure tracks 62 form a rail over which a port slider or pull tab (shown in FIG. 1 at 34) may be drawn in order to close or open the bottom.

Also shown are padded internal walls 22, and a cold pack pocket 40 on either side of the organ transplant sleeve 1. In the present embodiment, the cold pack pockets 40 are shaped to receive a removeable cold pack 50. The cold pack 50 may be, for example, a flexible plastic packet of ice, saline, vinyl-coated silica gel, hydroxyethyl cellulose, or other non-toxic refrigerant. It is advantageous if the outer walls 20 are at least partially rigid, so that the cold pack 50 may be inserted or withdrawn without disturbing the placement of an organ in the organ cavity 25.

In some embodiments, the top joint 18 may be pre-sealed and the external walls 20 may be substantially soft and flexible, to form a chilled pocket, which may be placed inside a body cavity to chill an organ in-situ during surgery.

While the various aspects of the invention are discussed with respect to individual embodiments, it will be appreciated that various aspects of one embodiment may be used with other embodiments and have been omitted for brevity. It will be appreciated further that various combinations may be made of the various embodiments discussed above. Thus, for example, in accordance with the teachings herein, an organ transplant container may include a transplant sleeve having a main body and at least one selectively closeable opening; and a connector attached to the transplant sleeve, the connector configured for attachment to a surgical frame. The transplant container may further include: the main body having a single wall vessel with an openable top end for inserting the organ into the main body, and a bottom end having at least one selectively openable opening disposed adjacent thereto for removing an organ from the main body; the main body having a top end having an opening for receiving an organ and a bottom end being openable to release the organ; the main body having a plurality of openings for accessing different parts of an organ when an organ is disposed in the main body; the main body being shaped to conform to a human kidney; at least one selectively openable opening disposed adjacent the bottom end has a series of perforations; at least one selectively openable opening disposed adjacent the bottom end having a slideable closure device; the at least one selectively openable opening being disposed adjacent the bottom end comprises a magnetic strip; the connector having a portion of a ratchet for retaining the transport sleet on a surgical frame; the connector having a swivel bearing permits the transplant sleeve to be swiveled while still hooked to a surgical frame; the transplant sleeve having a pocket for receiving a cooling material to thereby regulate temperature in the main body; the main body having a top and a bottom and wherein at least one selectively openable opening comprises an opening in the bottom of the main body; at least one selectively openable opening being located on a side of the main body; the main body further comprises cushioning material; main body having an inner wall attached to an outer wall, the inner wall being adapted to insulate an organ; and/or further having a temperature indicator located on the main body, and combinations thereof.

Likewise, a method of transporting and transplanting an organ may include: receiving a transplant sleeve having an organ disposed therein; attaching the transplant sleeve to a surgical frame; opening at least one selectable opening in the transplant sleeve to expose a vein or duct of the organ; and attaching the vein or duct to the patient while the organ remains in the transplant sleeve. The method may further include the transplant sleeve having a plurality of selectably openable openings; and/or opening a bottom portion of the transplant sleeve to release the organ from the transplant sleeve.

Thus there is disclosed a suspendable organ transplant sleeve system and methods of using the same. It will be appreciated that numerous modifications may be made without departing from the scope and spirit of this disclosure. The appended claims are intended to cover such modifications.

What is claimed is:

1. A method for handling an organ during transplantation, the method comprising:
   receiving a transplant sleeve having an organ disposed therein, the organ comprising a vein or duct;
   opening a first opening in the transplant sleeve to expose the vein or duct;
   attaching the vein or duct to a patient while the organ remains in the transplant sleeve; and
   creating an enlarged opening in the transplant sleeve to facilitate removal of the organ from the transplant sleeve after attachment of the vein or duct to a patient;
   removing the organ from the transplant sleeve after attaching the vein or duct to the patient.

2. The method according to claim 1, wherein the method further comprises attaching the transplant sleeve to a surgical frame to support the organ near the patient during transplantation.

3. The method according to claim 1, wherein the method further comprises opening a second opening in the transplant sleeve to release the organ from the transplant sleeve, wherein the second opening is connected to the first opening such that opening the first opening and the second opening creates the enlarged opening.

4. The method according to claim 1, wherein the method further comprises:
   opening a second opening in the transplant sleeve to expose a second vein or duct of the organ;
   attaching the second vein or duct to the patient while the organ remains in the transplant sleeve; and
   opening a third opening in the transplant sleeve wherein the third opening is connected to the first opening and to the second opening to thereby create the enlarged opening and to facilitate removal of the organ from the transplant sleeve.

5. The method according to claim 1, wherein the method further comprises monitoring the temperature of the organ while in the transplant sleeve via a temperature indicator which is attached to the transplant sleeve.

6. The method according to claim 1, wherein the method further comprises regulating the temperature of the organ via cooling material disposed in a pocket formed in the transplant sleeve.

7. An organ transplant container comprising:
   a transplant sleeve having a main body, at least one selectively closeable opening, and a pocket for receiving a cooling material to thereby regulate temperature in the main body; and
   a connector attached to the transplant sleeve, the connector configured for attachment to a surgical frame.

8. The organ transplant container of claim 7, wherein the main body comprises an inner wall which comprises an insulating material and which is attached to an outer wall, the inner wall being adapted to insulate an organ.

9. The organ transplant container of claim 7, further comprising a temperature indicator located on the main body.

10. The organ transplant container of claim 7, wherein the main body further comprises cushioning material positioned to extend around an organ when an organ is disposed in the transplant sleeve.

11. An organ transplant container comprising:
a transplant sleeve having a main body, at least one selectively closeable opening, and an inner wall which comprises an insulating material and which is attached to an outer wall, the inner wall being thereby adapted to insulate an organ; and
a connector attached to the transplant sleeve, the connector configured for attachment to a surgical frame.

12. The organ transplant container of claim 11, further comprising a pocket for receiving a cooling material to thereby regulate temperature of the main body.

13. The organ transplant container of claim 11, further comprising a temperature indicator located on the main body.

14. The organ transplant container of claim 11 wherein the main body further comprises cushioning material positioned to extend around an organ when an organ is disposed in the transplant sleeve.

15. The organ transplant container of claim 11, wherein the main body comprises a top end having an opening for receiving an organ and a bottom end having a selectively openable opening to release the organ.

16. The organ transplant container of claim 15, wherein the main body comprises a selectively openable port for accessing a vein or a duct of an organ when an organ is disposed in the main body.

17. The organ transplant container of claim 11, wherein the connector comprises a swivel bearing to permit the transplant sleeve to be swiveled while still hooked to a surgical frame.

18. An organ transplant container comprising:
a transplant sleeve having a main body configured for receiving an organ therein;
a first opening in the transplant sleeve which is selectively openable to expose a vein or duct of the organ and allow the vein or duct to be attached to a patient while the organ remains in the transplant sleeve;
a second opening in the transplant sleeve which is selectively openable to facilitate removal of the organ from the transplant sleeve;
wherein the second opening is connected to the first opening such that when the first opening and the second opening are both simultaneously open a single enlarged opening is created to facilitate removal of the organ from the transplant sleeve after attachment of the vein or duct to a patient.

19. The organ transplant sleeve of claim 18, wherein the transplant sleeve further comprises a connector attached to the transplant sleeve, the connector configured for attaching the transplant sleeve to a surgical frame to support the organ near a patient during transplantation.

20. The organ transplant sleeve of claim 18, wherein the transplant sleeve further comprises a cooling pocket having a cooling material disposed therein.

21. The organ transplant sleeve of claim 18, further comprising a third opening in the transplant sleeve which is selectively openable to expose a second vein or duct of the organ and allow the second vein or duct to be attached to a patient while the organ remains in the transplant sleeve, and wherein the second opening is connected to the third opening such that when the third opening and the second opening are both simultaneously open a single enlarged opening is created to facilitate removal of the organ from the transplant sleeve after attachment of the vein or duct to a patient.

* * * * *